(12) United States Patent
Hsu

(10) Patent No.: US 6,635,147 B1
(45) Date of Patent: Oct. 21, 2003

(54) METHOD FOR ANALYZING BORON-CONTAINING ALKALINE PULPING LIQUORS

(75) Inventor: Wu-hwa Wesley Hsu, West Hills, CA (US)

(73) Assignee: U.S. Borax Inc., Valencia, CA (US)

( * ) Notice: Subject to any disclaimer, the term of this patent is extended or adjusted under 35 U.S.C. 154(b) by 0 days.

(21) Appl. No.: 09/571,297

(22) Filed: May 14, 2000

(51) Int. Cl.⁷ .............................. D21C 3/02; D21C 7/12
(52) U.S. Cl. .............................. 162/49; 162/80; 162/82; 162/90
(58) Field of Search .............................. 162/49, 61, 62, 162/238, 80, 90, 82

(56) References Cited

U.S. PATENT DOCUMENTS 3,886,034 A    5/1975   Noreus
4,116,759 A  * 9/1978   Janson .......................... 162/32

FOREIGN PATENT DOCUMENTS

WO    WO 84/04552 B1    11/1984
WO       84/04552    *  11/1984

OTHER PUBLICATIONS

Camacho, "Specific Ion Electrode For Monitoring Mill Stream Soda Losses"; Southern Pulp and Paper Manufacture, Jun. 10, 1967, pp. 96–101.*

Camacho, "Specific Ion Electrode For Monitoring Mill Stream Losses"; Southern Pulp & Paper Manufacture, Jun. 1976, pp. 96–101, see p. 97, col. 3, lines 3–21.

MacDonald et al., "The Pulping of Wood", Pulp and Paper Manufacture, 2nd Ed., 1969, pp. 561–571, vol. I, McGraw Hill Book Company, New York, etc.

"Analysis of Sulfate Green and White Liquors", Standard J. 12, Recommended Method, Jun. 1961, Physical and Chemical Standards Committee, Technical Session, Canadian Pulp & Paper Association.

* cited by examiner

*Primary Examiner*—Steve Alvo
(74) *Attorney, Agent, or Firm*—Kurt R. Ganderup

(57) ABSTRACT

Chemical species (e.g., metaborate, carbonate, hydroxide and sulfide) in a boron-containing alkaline wood pulping liquor sample are determined quantitatively by (i) subjecting a first aliquot portion of the sample to a primary acid titration analysis to derive multiple equivalence points at different respective pH values; (ii) subjecting a second aliquot portion of the sample to an analysis to determine the quantitative presence of boron or sulfide ions therein, and then (iii) determining the quantitative presence in the sample of at least one of the chemical species. Wood pulping parameters may thus be determined on the basis of the quantitative presence of the chemical species to assist in process and/or quality control of the wood pulping operation. For example, the sample may be analyzed for boron content using calorimeter or atomic spectroscopy and/or analyzed for sulfide ion content using a secondary silver sulfide precipitation titration analysis, each of which may be conducted substantially simultaneously with the primary acid titration analysis.

16 Claims, 1 Drawing Sheet

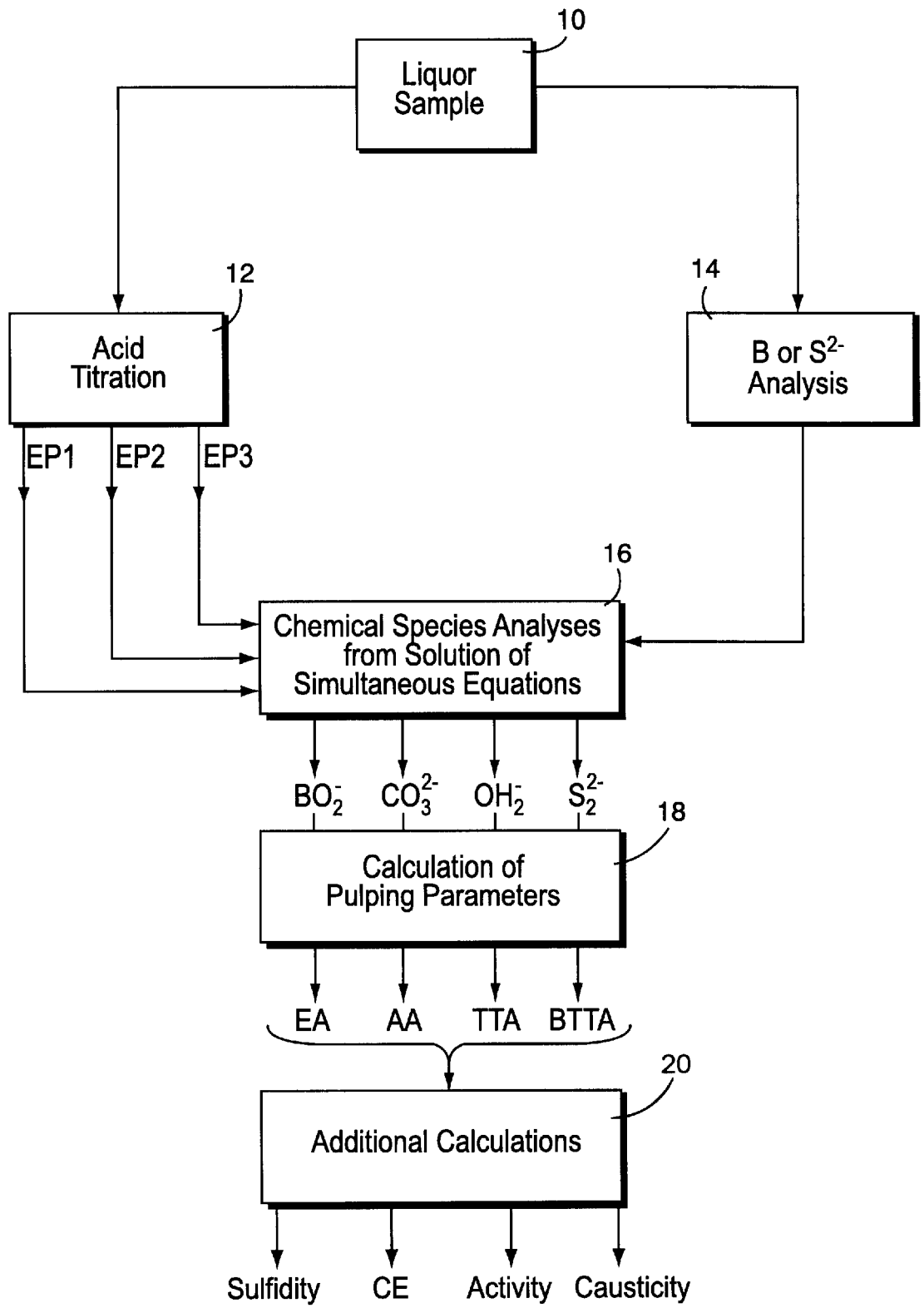

METHOD FOR ANALYZING BORON-CONTAINING ALKALINE PULPING LIQUORS

FIELD OF THE INVENTION

The present invention relates generally to methods for analyzing chemical species in wood pulping liquors. In especially preferred forms, the present invention relates to methods for analyzing quantitatively chemical species of boron-containing liquors associated with alkaline wood pulping processes.

BACKGROUND AND SUMMARY OF THE INVENTION

Alkaline pulping processes use a white liquor containing sodium hydroxide and sodium sulfide to extract fibers from wood chips in a high temperature pressurized digester. The black liquor discharged from the digester is evaporated and combusted. The black liquor combustion residue is then dissolved to form green liquor which is thereafter converted back to the white liquor through a lime cycle. The lime cycle typically includes a slaker in which the green liquor is causticized by lime to form a precipitated calcium carbonate mud, and a lime kiln in which the calcium carbonate mud is reconverted to lime by calcining.

In the above process, lime can be partially or entirely replaced by sodium borate. Sodium borate circulating through the plant process can automatically causticize the plant liquors by reacting with sodium carbonate to produce a trisodium borate ($Na_3BO_3$) which then reacts with water to generate sodium hydroxide. The use of borate could reduce or eliminate the cost of the lime cycle including equipment, energy and operation expenses. See, for example, U.S. Pat. No. 4,116,759 to Janson (the entire content of which is expressly incorporated hereinto by reference).

Measurement of white liquor alkali concentrations (hydroxide, sulfide and carbonate) is important to produce a uniform pulp quality and for stable digester operation. Determination of green liquor alkali concentrations is useful in causticizing control. Analysis of borate in both white and green liquors is necessary to control the amount of sodium borate needed to achieve the targeted autocausticizing effect. Therefore the ability to conduct these analyses efficiently and reliably plays a crucial role in promoting this new application.

The pulping industry has traditionally used an acid titration method, commonly referred to as the ABC method, to analyze hydroxide, carbonate and sulfide. See in this regard, Standard J.12, "Analysis of Sulphate Green and White Liquors", Canadian Pulp & Paper Association, (June, 1961), the entire content of which is expressly incorporated hereinto by reference. Generally, the ABC method involves a manual acid-base titration procedure with three equivalence points at different pH's. The equivalence point A (pH=10–11) detects hydroxide plus one-half sulfide; equivalence point B (pH=8–10) detects another one-half sulfide; and equivalence point C (pH=4.0–5.5) detects carbonate. It is a widely accepted and simple procedure which can be carried out manually, using pH sensitive color indicators. However, the presence of borate interferes with the conventional ABC method because borate is an effective buffer at a pH of 9 and thus obscures the equivalence point B.

Pulping liquors without borate can also be analyzed using an acid-base titration procedure on an autotitration system, again producing three pH equivalence points. In this case, equivalence point A (pH=10–11) detects hydroxide plus one-half sulfide; equivalence point B (pH=7.5–8.5) detects one-half of carbonate; and equivalence point C (pH=4.0–5.5) detects another one-half of sulfide and another one-half of carbonate. However, the presence of borate also interferes with this procedure because borate and carbonate have inseparable equivalence points at a pH in the range of 7.5 to 8.5. This makes the titration results indeterminate for all species because of the multi-step reactions and the interrelationship of the titration endpoints between the various species involved.

It would therefore be highly desirable if analytical methods could be provided which enable chemical species to be analyzed in boron-containing alkaline pulping liquors. It is towards fulfilling such a need that the present invention is directed.

Broadly, therefore, the present invention is embodied in methods by which borate-containing pulping liquors can be analyzed. The methods of the present invention therefore overcomes many (if not all) of the problems associated with analyzing borate-containing liquors by conventional techniques. Most preferably, the analysis methods of the present invention are automated for increased simplicity and reliability.

More particularly, the present invention provides an improved method for analyzing boron-containing alkaline wood pulping liquors for the determination of sulfide, hydroxide, carbonate and boron, as well as other useful solution properties which are dependent on these chemical analyses and are important to the operation of a pulping process. The method of the present invention most preferably comprises use of the acid titration procedure in concert with the determination of either boron or sulfide by other analytical methods and integration of the resulting data through a series of:equations to determine the sulfide, hydroxide, carbonate and boron content of the solution. Preferably, the acid titration procedure is carried out on an automatic titration system. Most preferably sulfide is measured by precipitation as silver sulfide, using a second autotitration unit, and the two autotitration units are coupled using a programmable unit such that the acid and sulfide analyses can carried out automatically and the results can be automatically input and analyzed using a series of equations, such that the desired results are provided automatically by the instrument.

In especially preferred embodiments of the present invention, chemical species (e.g., metaborate, carbonate, hydroxide and sulfide) in a boron-containing alkaline wood pulping liquor sample are determined quantitatively by (i) subjecting a first aliquot portion of the sample to a primary acid titration analysis to derive multiple equivalence points at different respective pH values; (ii) subjecting a second aliquot portion of the sample to an analysis to determine the quantitative presence of boron or sulfide ions therein, and then (iii) determining the quantitative presence in the sample of at least one of the chemical species. Wood pulping parameters may thus be determined on the basis of the quantitative presence of the chemical species to assist in process and/or quality control of the wood pulping operation. Alternatively, wood pulping parameters may be derived based on the analytical results of steps (i) and (ii), without determining the quantitative presence of the chemical species.

For example, the sample may be analyzed for boron content using various techniques, such as, for example, colorimetry or atomic spectroscopy (e.g., flame atomic adsorption (FM) or inductively coupled plasma (ICP)) and/ or analyzed for sulfide ion content using secondary silver sulfide precipitation titration analysis. These techniques may be conducted substantially concurrently with the primary acid titration analysis. Most preferably sulfide ion content is analyzed using a secondary silver sulfide precipitation analysis and the primary acid titration analysis and secondary silver sulfide precipitation analysis are conducted substantially simultaneously in parallel on separate independent autotitration units which are electronically coupled and preprogrammed such that all necessary analytical results and solution properties are calculated and reported automatically.

These and other aspects and advantages will become more apparent after careful consideration is given to the following detailed description of the preferred exemplary embodiments thereof.

BRIEF DESCRIPTION OF THE ACCOMPANYING DRAWING

Reference will hereinafter be made to the accompanying drawing FIGURE which is a schematic presentation of the exemplary steps employed for the method according to the present invention.

DETAILED DESCRIPTION OF THE INVENTION

With reference to the accompanying drawing FIGURE, the methods of the present invention involve initially collecting a sample of the pulping liquor in step 10. Respective aliquot portions of the liquor sample are then subjected in any order, but preferably substantially immediately, to the parallel analyses identified in steps 12 and 14—namely, an acid titration (step 12) and boron or sulfide analyses (step 14). Most preferably, when step 14 measures sulfide, the analyses of steps 12 and 14 should occur substantially simultaneously, but certainly within a reasonable sequential time period which minimizes any potential oxidation of sulfide in the sample.

According to the method of this invention, the acid titration step 12 is carried out by suitable means, such as an automatic titration system (autotitrator) which provides three pH inflection data points as indicated in Table 1 using well known techniques. The acid titration involves applying a series of sequential pH titration steps to a single sample of solution as noted in Table 1 below:

TABLE 1 pH Inflection Data Points

| pH | Chemical Reaction |
|---|---|
| 10.0–11.0 | $OH^- + H^+ \rightarrow H_2O$ |
| 10.0–11.0 | $S^{-2} + H^+ \rightarrow HS^-$ |
| 7.5–8.5 | $CO_3^{-2} + H^+ \rightarrow HCO_3^-$ |
| 7.5–8.5 | $B(OH)_4^- + H^+ \rightarrow H_3BO_3 + H_2O$ |
| 4.0–5.5 | $HS^- + H^+ \rightarrow H_2S$ |
| 4.0–5.5 | $HCO_3^- + H^+ \rightarrow H_2CO_3$ |

The acid titration step 12 of a sample of boron-containing alkaline wood pulping liquor is most preferably carried out using an autotitrator instrument, as the endpoints may be obscured and imprecise if this titration is carried out manually. The titration may be carried out on any suitable commercially available autotitration unit, such as the Brinkmann 751 titration system. Care should be taken not to expose the collected alkaline liquor sample to the atmosphere. Thus, the sample should be titrated substantially immediately upon collection to avoid the oxidation of sulfide. The sample is titrated with a suitable acid, such as hydrochloric acid (HCl), to three sequential pH inflection endpoints at about pH 10.0–11.0, pH 7.5–8.5, and pH 4.0–5.5.

The first endpoint (EP1) at pH 10.0–11.0 results from the titration of the hydroxide and half of the sulfide. (Eqs. 1 and 2)

$$OH^- + H^+ \rightarrow H_2O \qquad (Eq. 1)$$

$$S^{-2} + H^+ \rightarrow HS^- \qquad (Eq. 2)$$

The second endpoint (EP2) of the acid titration results from the titration of half the carbonate and the metaborate. (Eqs. 3 and 4)

$$CO_3^{2-} + H^+ \rightarrow HCO_3^- \qquad (Eq. 3)$$

$$BO_2^- + H_3O^+ \rightarrow B(OH)_3 \text{ or}$$

$$B(OH)_4^- + H^+ \rightarrow H_3BO_3 + H_2O \qquad (Eq. 4)$$

The third endpoint (EP3) results from the titration of the second half of the carbonate and the second half of sulfide. (Eq. 5 and 6)

$$HCO_3^- + H^+ \rightarrow H_2CO_3 \qquad (Eq. 5)$$

$$HS^- + H^+ \rightarrow H_2S \qquad (Eq. 6)$$

According to the present invention, another (fourth) data point, such as the boron or sulfide content of the solution, is provided by other analytical techniques in step 14. For example, boron may be determined by any suitable method, such as by colorimetry or atomic spectroscopy (e.g. flame atomic absorption (FAA) or inductively coupled plasma (ICP)). Alternatively or additionally, sulfide ion content may be determined by various analytical methods, such as by precipitation of silver sulfide analysis.

For best results, the acid titration step of the analysis should be carried out promptly after the sample is collected, due to the likelihood of chemical degradation of the chemical species in solution, particularly the oxidation of sulfide ion. Similarly, if the analytical method being used includes sulfide analysis in step 14, such as by sulfide precipitation titration, the sulfide analysis should also be carried out promptly after the sample is collected, in order to avoid undesirable degradation of the solution contents. However, if the analytical method being used alternatively includes boron analysis in step 14, such as by colorimetry or atomic spectroscopy, the boron analysis does not need to be done immediately.

The boron or sulfide analysis obtained in step 14 and the three pH data points EP1, EP2 and EP3 obtained by acid titration in step 12 are then employed in step 16 to determine algorithmically the levels of sulfide, hydroxide, carbonate and boron in the solution, through the solution of a series of simultaneous equations. That is, the concentrations of the four species of interest (i.e., hydroxide, sulfide, carbonate and metaborate) are calculated from the four data points obtained as described above.

As described above, one embodiment of the present invention involves the determination of the boron concentration in the sample by any suitable analytical method. The boron concentration and the volumes of titrant from the three acid titration endpoints are then used to derive the concentration of metaborate ($BO_2^-$), carbonate ($CO_3^{2-}$), hydroxide ($OH^-$) and sulfide ($S^{2-}$) from the following equations:

$BO_2^-$ = Metaborate (as $Na_2O$) = $V_{H,B} * N *$ Factor = $B * 3.7 * 10^{-4} * F$ $CO_3^{2-}$ = Carbonate (as $Na_2O$) = $2 * (EP2 - EP1 - V_{H,B}) * N * F$ $OH^-$ = Hydroxide (as $Na_2O$) = $(2 * EP2 - EP3 - V_{H,B}) * N * F$ $S^{2-}$ = Sulfide (as $Na_2O$)
= $2 * [(EP3 - EP2) - (EP2 - EP1 - V_{H,B})] * N * F$
= $2 * (EP3 - 2EP2 + EP1 + V_{H,B}) * N * F$ where:
B=boron (g/ml), obtained from FAA, ICP or other methods;
EP=Volume (ML) of HCl at the first endpoint;
EP2=Volume (mL) of HCl at the second endpoint;
EP3=Volume (mL) of HCl at the third endpoint;
N=Normality of the titrant HCl;
$V_{H,B}$=Volume (mL) of HCl needed to titrate the metaborate;

={[(B/1000)/10.811]*4}/N=B*3.7*10^{-4}/N; and

F is a factor for converting chemical species or pulping parameters to their equivalent $Na_2O$ amount. For solution concentrations in, grams per liter (g/L) F is given by the equation:

$F = (1/V_{ats}) * (1000 \text{ mL}/1 \text{ L}) * (0.062 \text{ g } Na_2O/2 \text{ mEq})$ where $V_{ats}$=Volume (mL) of the acid titration sample.

The factor, F, may be easily converted for expression of solution concentrations in other units. The factor F is used to convert chemical species or pulping parameters to their equivalent $Na_2O$ amount. The following values are based upon the sample size of 4 ml for the acid titration:

| Unit | Factor, F |
|---|---|
| g/L | 7.75 |
| lb/gal | 0.0645 |
| lb/ft³ | 0.484 |

By way of example, the factor F for the units g/L may be derived from the equation: F=(¼ m/L)(1000 mL/1L)(0.062 g $Na_2O$/2 mEq).

Pulping parameters for process and quality control in conventional wood pulping processes may be determined in step 18. More specifically, these pulping parameters are derived from the levels of chemical species or directly from the boron concentration and the volumes of titrant from the three acid titration endpoints, according to the following equations:

The Effective Alkali (EA), which represents $OH^- + \frac{1}{2}S^{2-}$, expressed as $Na_2O$ is determined from the equation:

EA=Effective Alkali (as $Na_2O$)=$OH^- + \frac{1}{2}S^{2-}$=$EP1*N*F$

The Active Alkali (AA) expressed as $Na_2O$ is determined from the equation:

AA = Active Alkali (as $Na_2O$) = $OH^- + S^{2-}$
= $[EP3 - 2*(EP2 - EP1 - V_{H,B}) - ]*N*F$
= $[EP3 - 2*EP2 + 2*EP1 + V_{H,B}]*N*F$ The Total Titratable Alkali excluding Metaborate (TTA) expressed as $Na_2O$ is determined from the equation:

TTA = Total Titratable Alkali excluding Metaborate (as $Na_2O$)
= $OH^- + S^{2-} + CO_3^{2-}$
= $(EP3 - V_{H,B}) * N * F$ The Total Titratable Alkali including Metaborate (BTTA) expressed as $Na_2O$ is determined by the equation:

BTTA = Total Titratable Alkali including Metaborate (as $Na_2O$)
= $OH^- + S^{2-} + CO_3^{2-} + BO_2^-$
= $EP3 * N * F$ Additional pulping parameters may then be determined in step 20 using the following formulas:

Sulfidity of the green liquor=$(S^{2-}/TTA)*100\%$

Sulfidity of the white liquor=$(S^{2-}/AA)*100\%$

CE=Causticizing Efficiency=$[OH^-/(OH^- + CO_3^{2-})]*100$

Activity=$(AA/TTA)*100\%$

Causticity=$(OH^-/TTA)100\%$

Analytical step 14 in accordance with the methods of the present invention may alternatively (or additionally) measure the sulfide content of the sample, such as by silver sulfide ($Ag_2S$) precipitation titration. Sulfide precipitation titration may be carried out manually or by autotitration. In the sulfide precipitation procedure, the sample is first diluted and dissolved in an ammonia solution and then titrated with silver nitrate ($AgNO_3$). Silver ion and ammonia form a very stable complex and thus only those ions with a, more stable precipitate will form. A sulfide ion-specific electrode is used to detect the endpoint. This procedure effectively removes potential interference of other ions and allows the sulfide to be titrated according to the following equation:

$2Ag^+ + S^{2-} \rightarrow Ag_2S$ (Eq. 7)

The volume of the titrant ($AgNO_3$) at the endpoint of the sulfide precipitation ($Ag_2S$) titration and the volumes of titrant from the three acid titration endpoints are used to derive the concentration of metaborate ($BO_2^-$), carbonate ($CO_3^{2-}$), hydroxide ($OH^-$) and sulfide ($S^{2-}$) from the equations as noted below:

$V_{H,S} = [(N_{AgNO3} * V_{AgNO3}/V_{sample})] * 4/N_{HCl}$ (Eq. 8)

where: $V_{H,S}$ is the volume of the HCl needed to titrate the sulfide; $N_{AgNO3}$ is the normality of the AgNO3 at the endpoint of the precipitation titration; $V_{AgNO3}$ is the volume (ml) of the $AgNO_3$ at the endpoint of the precipitation titration; $V_{sample}$ is the volume of the liquor sample and $N_{HCl}$ is the normality of the titrant HCl in acid-titration.

$S^{2-} = V_{H,S} * N *$ Factor (Eq. 9)

$CO_3^{2-} = 2*(EP3-EP2-0.5V_{H,S})*N*$Factor (Eq. 10)

$$BO_2^- = EP2-EP1-0.5CO_3^{2-} = (2EP2-EP1-EP3+0.5V_{H_2S})*N*F \quad \text{(Eq. 11)}$$

or: Boron (ug/ml)=$(2EP2-EP1-EP3+0.5V_{H_2S})*N*2702.75$ OH$^-$=
$(EP1-0.5V_{H_2S})*N*$Factor  (Eq. 12)

wherein EP1, EP2 and EP3 are as defined previously, and the sulfide, carbonate, metaborate and hydroxide species are expressed on the basis of $Na_2O$.

The pulping parameters in step 18 are calculated from the levels of chemical species or directly from EP1, EP2, EP3 and $V_{H_2S}$. They are expressed on the basis of $Na_2O$.

$$EA = OH^- + \tfrac{1}{2}S^{2-} = EP1*N*F \quad \text{(Eq. 13)}$$

$$AA = OH^- + S^{2-} = (EP1+0.5*V_{H_2S})*N*F \quad \text{(Eq. 14)}$$

$$TTA = OH^- + S^{2-} + CO_3^{2-} = (2*EP3-2*EP2-0.5VH_{H_2S}+EP1)*N*F \quad \text{(Eq. 15)}$$

$$BTTA = OH^- + S^{2-} + CO_3^{2-} + BO_2^- = EP3*N*F \quad \text{(Eq. 16)}$$

Additional pulping parameters in step 20 may then be derived from the following equations.

Sulfidity of the green liquor=$(S^{2-}/TTA)*100\%$ (Eq. 17)

Sulfidity of the white liquor=$(S^{2-}/AA)*100\%$ (Eq. 18)

$CE=[OH^-/(OH^-+CO_3^{2-})]*100$  (Eq. 19)

Activity=$(AA/TTA)*100\%$  (Eq. 20)

Causticity=$(OH^-/TTA)*100\%$  (Eq. 21)

Most preferably, the acid titration and sulfide precipitation titration are each carried out on separate independent autotitration units which are electronically coupled, such as a Metrohm 751 Double Titrator, with the above equations (i.e., Eqs. 8–21) preprogrammed into the instrument such that all necessary analytical results and solution properties are calculated and reported automatically. The two titration procedures are most preferably carried out substantially simultaneously in parallel on the separate, but electronically coupled, autotitration units using separate aliquot portions of the same liquor sample solution. The results of the titration can be fed into a programmable computer having the pulping parameter equations preprogrammed therein so as to achieve a read out as to the pulping parameters to assist in process and/or quality control procedures, and the like.

The present invention will be further understood by reference to the following non-limiting Examples.

EXAMPLES

Stock solutions of the four major components of white and green pulping liquors, sodium hydroxide, sodium carbonate, sodium sulfide and sodium metaborate were prepared in the laboratory. All water used in these experiments was ultra pure water with a resistance of 18.2 megohm/cm or greater and has been sparged with helium. 105 grams of anhydrous sodium carbonate, $Na_2CO_3$, was added to 500 ml of water and allowed to dissolve. 240 grams of sodium hydroxide pellets, NaOH, was slowly added to 500 ml of water in a plastic bottle which was in an ice bath and stirred until dissolved. 220 grams of sodium metaborate, $Na_2O \cdot B_2O_3 \cdot 4H_2O$, was added to 500 ml of water in a plastic bottle and allowed to dissolve. 207 grams of sodium sulfide, $Na_2S \cdot 9H_2O$ was added to 500 ml of water in a brown plastic bottle and allowed to slowly dissolve. (Note: it is best to let this solution set overnight to slowly dissolve and to invert the bottle only once or twice to promote mixing). The sodium sulfide crystals were first rinsed off with water and then blotted dry before weighing. The stock solutions were standardized daily by titrating an aliquot of each solution with 1.0N HCl.

A. Sodium Carbonate

Preparation of $Na_2CO_3$ stock solution:
Standardization using HCl: Dilute 105 gm $Na_2CO_3$ with water to 500 mL

| Rep. | Aliquot of stock (mL) | Titrant at 1st endpoint (mL) | Titrant at 2nd endpoint * (mL) | Conc. $Na_2CO_3$ (M) | (g/L) | (%) |
|---|---|---|---|---|---|---|
| 1 | 3 | 5.952 | 11.850 | 1.98 | 209 | 20.9 |
|   | Mean | 5.952 | 11.850 | 1.975 | 209 | 20.9 |

* Consumed up to the second endpoint

B. Sodium Metaborate

Preparation of $NaBO_2$ stock solution:
Standardization using HCl: Dilute 220 gm $Na_2OB_2O_3 \cdot 4H_2O$ with water to 500 mL

| Rep. | Aliquot of Stock (mL) | Titrant (mL) | Conc. $NaBO_2$ (M) | (g/L) | (%) |
|---|---|---|---|---|---|
| 1 | 1 | 3.721 | 3.72 | 245 | 24.5 |
|   | Mean | 3.721 | 3.721 | 245 | 24.5 |

C. Sodium Hydroxide

Preparation of NaOH stock solution:
Standardization using HCl: Dilute 240 gm NaOH with water to 500 mL

| Rep. | Aliquot of stock (mL) | Titrant (mL) | Conc. NaOH (M) | (g/L) | (%) |
|---|---|---|---|---|---|
| 1 | 3 | 32.755 | 10.92 | 437 | 43.7 |
|   | Mean | 32.755 | 10.918 | 437 | 43.7 |

D. Sodium Sulfide

Preparation of $Na_2S$ stock solution:
Standardization using HCl: Dilute 207 gm $Na_2S \cdot 9H_2O$ with water to 500 mL

| Rep. | Aliquot of stock (mL) | Titrant at 1st endpoint (mL) | Titrant at 2nd endpoint * (mL) | Conc. $Na_2S$ (M) | (g/L) | (%) |
|---|---|---|---|---|---|---|
| 1 | 4 | 6.111 | 12.227 | 1.53 | 119 | 11.9 |
|   | Mean | 6.111 | 12.227 | 1.528 | 119 | 11.9 |

* Consumed up to the second endpoint

After standardization of the stock solutions, synthetic green and white liquor samples were made. The liquor samples were similar in composition to the green and white liquor used in pulping mills at various levels of borate addition.

For synthetic white liquor samples, 15 ml of the stock sodium hydroxide solution, 5 ml of the stock sodium carbonate solution, 15 ml of the stock sodium sulfide solution and various amounts of the stock sodium borate solution were added into 50 ml plastic vessels. Each solution was brought to a final volume of 50 ml with water and mixed thoroughly to make a synthetic white liquor sample.

The synthetic white liquor sample was then analyzed by a precipitation titration followed by an acid titration on a Brinkmann 751 double titration system. The precipitation titration was done by pipetting a 1 ml aliquot of the synthetic white liquor into 200 ml 1 N ammonium hydroxide and then titrating with 0.1 N silver nitrate. The electrode used in the precipitation titration was a Brinkmann Ag Titrode. The acid titration was done by pipetting a 4 ml aliquot of the liquor into roughly 175 ml water and then titrating with 1.0 N hydrochloric acid. The electrode used in the acid titration is a Brinkmann Combination pH Glass Electrode. Four endpoints were obtained from the two titrations to calculate the chemical components and pulping parameters. The titration endpoints are given below:

| | | Experimental conditions | | | | | | | |
|---|---|---|---|---|---|---|---|---|---|
| | | NaOH | | | $Na_2CO_3$ | | | $Na_2S$ | |
| | Liquor Type* | Ml, volume of the stock | % | N, Normality of NaOH in sample | ml, volume of the stock | % | N | ml, volume of the stock | % | N |
| #1 | White liquor | 15 | 13.0 | 3.2 | 5 | 2.1 | 0.4 | 15 | 3.6 | 0.9 |
| #2 | White liquor | 15 | 13.0 | 3.2 | 5 | 2.1 | 0.4 | 15 | 3.6 | 0.9 |
| #3 | White liquor | 15 | 13.0 | 3.2 | 5 | 2.1 | 0.4 | 15 | 3.6 | 0.9 |
| #4 | White liquor | 15 | 13.0 | 3.2 | 5 | 2.1 | 0.4 | 15 | 3.6 | 0.9 |
| #5 | White liquid | 15 | 13.0 | 3.2 | 5 | 2.1 | 0.4 | 15 | 3.6 | 0.9 |
| #6 | White liquor | 15 | 13.0 | 3.2 | 5 | 2.1 | 0.4 | 15 | 3.6 | 0.9 |
| #7 | White liquid | 15 | 13.0 | 3.2 | 5 | 2.1 | 0.4 | 15 | 3.6 | 0.9 |
| #8 | White liquor | 15 | 130 | 3.2 | 5 | 2.1 | 0.4 | 15 | 3.6 | 0.9 |
| #9 | White liquor | 15 | 13.0 | 3.2 | 5 | 2.1 | 0.4 | 15 | 3.6 | 0.9 |
| #10 | White liquor | 15 | 13.0 | 3.2 | 5 | 2.1 | 0.4 | 15 | 3.6 | 0.9 |

| | | Experimental conditions $NaBO_2$ | | | V, Endpoints | | | |
|---|---|---|---|---|---|---|---|---|
| | Liquor Type* | ml, volume of the stock | % | N | V, AgNO3 ml | A (EP1) V, HCl ml | B (EP2) V, HCl ml | C (EP3) V, HCl ml |
| #1 | White liquor | 0 | 0.0 | 0.00 | 8.612 | 15.079 | 15.909 | 18.546 |
| #2 | White liquor | 0 | 0.0 | 0.00 | 8.437 | 14.749 | 15.585 | 18.164 |
| #3 | White liquor | 4 | 1.9 | 0.29 | 8.450 | 14.932 | 17.001 | 19.568 |
| #4 | White liquor | 4 | 1.9 | 0.29 | 8.603 | 14.818 | 16.845 | 19.415 |
| #5 | White liquid | 8 | 3.8 | 0.57 | 8.481 | 14.733 | 17.991 | 20.573 |
| #6 | White liquor | 8 | 3.8 | 0.57 | 8.397 | 14.724 | 17.967 | 20.559 |
| #7 | White liquid | 12 | 5.7 | 0.86 | 8.373 | 14.792 | 19.247 | 21.855 |
| #8 | White liquor | 12 | 5.7 | 0.86 | 8.311 | 14.760 | 19.213 | 21.823 |
| #9 | White liquor | 15 | 7.1 | 1.08 | 8.655 | 14.757 | 20.114 | 22.735 |
| #10 | White liquor | 15 | 7.1 | 1.08 | 8.615 | 14.750 | 20.103 | 22.726 |

For synthetic green liquor samples, 2.5 ml of the stock sodium hydroxide solution, 15 ml of the stock sodium sulfide solution, and various amounts of the stock sodium borate solution were added into 50 ml plastic vessels. As for sodium carbonate, due to its high concentration in green liquor, 7.1000 grams of anhydrous sodium carbonate was added and dissolved by additional water. Each solution was brought to a final volume of 50 ml with water and mixed thoroughly.

The concentration of sodium carbonate in a solution prepared by dissolving 7.1000 grams of anhydrous sodium carbonate in 50 ml water (final volume) was determined daily by titrating with 1.0 N HCl. An example of this determination is as follows:

| Preparation of 14.2% $Na_2CO_3$: Standardization using HCl: | | Dilute 7.1 gm $Na_2CO_3$ with water to 50 ml | | | | |
|---|---|---|---|---|---|---|
| | Aliquot of stock | Titrant at 1$^{st}$ endpoint | Titrant at 2nd endpoint * | Conc. Na2CO3 | | |
| Rep. | (mL) | (mL) | (mL) | (M) | (g/L) | (%) |
| 1 | 3 | 4.118 | 8.197 | 1.37 | 145 | 14.5 |
| Mean | | 4.118 | 8.197 | 1.366 | 145 | 14.5 |

* Consumed up to the second endpoint

The synthetic green liquor was then analyzed by a precipitation titration followed by an acid titration on a Brinkmann 751 double titration system. The precipitation titration was done by pipetting a 1 ml aliquot of the synthetic white liquor into 200 ml 1 N ammonium hydroxide and then titrating with 0.1 N silver nitrate. The electrode used in the precipitation titration was a Brinkmann Ag Titrode. The acid titration was done by pipetting a 4 ml aliquot of the liquor into roughly 175 ml water and then titrating with 1.0 N hydrochloric acid. The electrode used in the acid titration is a Brinkmann Combination pH Glass Electrode. Four endpoints were obtained from the two titrations to calculate the chemical components and pulping parameters. The titration endpoints are given below:

results are tabulated as follows:

| | Liquor Type* | NaOH | | | $Na_2CO_3$ gm, Na2CO3 * | | | $Na_2S$ | | | $NaBO_2$ | | | V, endpoints | | | |
|---|---|---|---|---|---|---|---|---|---|---|---|---|---|---|---|---|---|
| | | | | | | | | | | | | | | V, AgNO3 | A (EP1) V, HCl | B (EP2) V, HCl | C (EP3) V, HCl |
| | | ml | % | N | | % | N | ml | % | N | ml | % | N | ml | ml | ml | ml |
| #1 | Green liquor | 2.5 | 2.2 | 0.5 | 7.100 | 14.5 | 2.7 | 15 | 3.6 | 0.9 | 0 | 0.0 | 0.00 | 9.024 | 4.185 | 9.602 | 16.840 |
| #2 | Green liquor | 2.5 | 2.2 | 0.5 | 7.100 | 14.2 | 2.7 | 15 | 3.6 | 0.9 | 0 | 0.0 | 0.00 | 8.832 | 4.186 | 9.590 | 16.839 |
| #3 | Green liquor | 2.5 | 2.2 | 0.5 | 7.100 | 14.2 | 2.7 | 15 | 3.6 | 0.9 | 4 | 2.0 | 0.30 | 8.803 | 4.128 | 10.928 | 18.269 |
| #4 | Green liquor | 2.5 | 2.2 | 0.5 | 7.100 | 14.2 | 2.7 | 15 | 3.6 | 0.9 | 4 | 2.0 | 0.30 | 8.707 | 4.120 | 10.891 | 18.197 |
| #5 | Green liquor | 2.6 | 2.2 | 0.5 | 7.100 | 14.2 | 2.7 | 15 | 3.6 | 0.9 | 8 | 3.9 | 0.60 | 9.219 | 4.065 | 12.175 | 19.509 |
| #6 | Green liquor | 2.5 | 2.2 | 0.5 | 7.100 | 4.2 | 2.7 | 15 | 3.6 | 0.9 | 8 | 3.9 | 0.60 | 9.246 | 4.067 | 12.119 | 19.485 |
| #7 | Green liquor | 2.5 | 2.2 | 0.5 | 7.100 | 14.2 | 2.7 | 15 | 3.6 | 0.9 | 12 | 5.9 | 0.89 | 9.073 | 4.003 | 13.189 | 20.434 |
| #8 | Green liquor | 2.6 | 2.2 | 0.5 | 7.100 | 14.2 | 2.7 | 15 | 3.6 | 0.9 | 12 | 5.9 | 0.89 | 8.882 | 4.005 | 13.092 | 20.358 |
| #9 | Green liquor | 2.5 | 2.2 | 0.5 | 7.100 | 14.2 | 2.7 | 15 | 3.6 | 0.9 | 15 | 7.3 | 1.12 | 8.973 | 4.000 | 14.151 | 21.538 |
| #10 | Green liquor | 2.5 | 2.2 | 0.5 | 7.100 | 14.2 | 2.7 | 15 | 3.6 | 0.9 | 15 | 7.3 | 1.12 | 9.243 | 4.014 | 14.208 | 21.587 |

The theoretical percents of the four components in the green and white liquor samples can be calculated and compared to the percents of the four components as obtained from the titration. A table of this comparison is given below: The comparison of theoretical values and the experimental

|  | NaOH (as g/L Na$_2$O) | | Na$_2$CO$_3$ (as g/L Na$_2$O) | | Na$_2$S (as g/L Na$_2$O) | | NaBO$_2$ (as g/L Na$_2$O) | |
|---|---|---|---|---|---|---|---|---|
|  | Theoretical | Experimental | Theoretical | Experimental | Theoretical | Experimental | Theoretical | Experimental |
| White Liquor | | | | | | | | |
| #1 | 101.5 | 103.5 | 12.1 | 14.1 | 28.4 | 26.8 | 0.0 | −0.6 |
| #2 | 101.5 | 101.2 | 12.1 | 13.7 | 28.4 | 26.3 | 0.0 | −0.4 |
| #3 | 101.5 | 102.6 | 12.1 | 13.5 | 28.4 | 26.3 | 9.2 | 9.3 |
| #4 | 101.5 | 101.5 | 12.1 | 13.1 | 28.4 | 26.8 | 9.2 | 9.2 |
| #5 | 101.5 | 101.0 | 12.1 | 13.6 | 28.4 | 26.4 | 18.5 | 18.4 |
| #6 | 101.5 | 101.0 | 12.1 | 14.0 | 28.4 | 26.1 | 18.5 | 18.1 |
| #7 | 101.5 | 101.6 | 12.1 | 14.4 | 28.4 | 26.1 | 27.7 | 27.3 |
| #8 | 101.5 | 101.5 | 12.1 | 14.6 | 28.4 | 25.9 | 27.7 | 27.2 |
| #9 | 101.5 | 100.9 | 12.1 | 13.7 | 28.4 | 26.9 | 34.6 | 34.7 |
| #10 | 101.5 | 100.9 | 12.1 | 13.8 | 28.4 | 26.8 | 34.6 | 34.6 |
| Green Liquor | | | | | | | | |
| #1 | 16.9 | 18.4 | 83.1 | 84.1 | 28.4 | 28.1 | 0.0 | −0.1 |
| #2 | 16.9 | 18.7 | 83.1 | 84.9 | 28.4 | 27.5 | 0.0 | −0.6 |
| #3 | 16.9 | 18.3 | 83.1 | 86.4 | 28.4 | 27.4 | 9.2 | 9.5 |
| #4 | 16.9 | 18.4 | 83.1 | 86.1 | 28.4 | 27.1 | 9.2 | 9.4 |
| #5 | 16.9 | 17.2 | 83.1 | 85.0 | 28.4 | 28.7 | 18.5 | 20.4 |
| #6 | 16.9 | 17.1 | 83.1 | 85.4 | 28.4 | 28.8 | 18.5 | 19.7 |
| #7 | 16.9 | 16.9 | 83.1 | 84.1 | 28.4 | 28.2 | 27.7 | 29.2 |
| #8 | 16.9 | 17.2 | 83.1 | 85.0 | 28.4 | 27.6 | 27.7 | 27.9 |
| #9 | 16.9 | 17.0 | 83.1 | 86.6 | 28.4 | 27.9 | 34.6 | 35.4 |
| #10 | 16.9 | 16.7 | 83.1 | 85.6 | 28.4 | 28.8 | 34.6 | 36.2 |

|  | EA (as g/L Na$_2$O) | | AA (as g/L Na$_2$O) | | TTA (as g/L Na$_2$O) | | BTTA (as g/L Na$_2$O) | |
|---|---|---|---|---|---|---|---|---|
|  | Theoretical | Experimental | Theoretical | Experimental | Theoretical | Experimental | Theoretical | Experimental |
| White Liquor | | | | | | | | |
| #1 | 115.7 | 116.9 | 113.6 | 117.5 | 142.1 | 144.3 | 142.1 | 143.7 |
| #2 | 115.7 | 114.3 | 113.6 | 114.9 | 142.1 | 141.1 | 142.1 | 140.8 |
| #3 | 115.7 | 115.7 | 113.6 | 116.1 | 142.1 | 142.4 | 151.3 | 151.7 |
| #4 | 115.7 | 114.8 | 113.6 | 114.5 | 142.1 | 141.3 | 151.3 | 150.5 |
| #5 | 115.7 | 114.2 | 113.6 | 114.6 | 142.1 | 141.0 | 160.5 | 159.4 |
| #6 | 115.7 | 114.1 | 113.6 | 115.1 | 142.1 | 141.2 | 160.5 | 159.3 |
| #7 | 115.7 | 114.6 | 113.6 | 116.0 | 142.1 | 142.0 | 169.7 | 169.4 |
| #8 | 115.7 | 114.4 | 113.6 | 116.0 | 142.1 | 141.9 | 169.7 | 169.1 |
| #9 | 115.7 | 114.4 | 113.6 | 114.6 | 142.1 | 141.5 | 176.7 | 176.2 |
| #10 | 115.7 | 114.3 | 113.6 | 114.7 | 142.1 | 141.6 | 176.7 | 176.1 |
| Green Liquor | | | | | | | | |
| #1 | 31.1 | 32.4 | 100.0 | 102.5 | 128.4 | 130.6 | 128.4 | 130.5 |
| #2 | 31.1 | 32.4 | 100.0 | 103.6 | 128.4 | 131.1 | 128.4 | 130.5 |
| #3 | 31.1 | 32.0 | 100.0 | 104.7 | 128.4 | 132.1 | 137.6 | 141.6 |
| #4 | 31.1 | 31.9 | 100.0 | 104.5 | 128.4 | 131.6 | 137.6 | 141.0 |
| #5 | 31.1 | 31.5 | 100.0 | 102.1 | 128.4 | 130.8 | 146.9 | 151.2 |
| #6 | 31.1 | 31.5 | 100.0 | 102.5 | 128.4 | 131.3 | 146.9 | 151.0 |
| #7 | 31.1 | 31.0 | 100.0 | 101.0 | 128.4 | 129.2 | 156.1 | 158.4 |
| #8 | 31.1 | 31.0 | 100.0 | 102.2 | 128.4 | 129.8 | 156.1 | 157.8 |
| #9 | 31.1 | 31.0 | 100.0 | 103.6 | 128.4 | 131.5 | 163.0 | 166.9 |
| #10 | 31.1 | 31.1 | 100.0 | 102.3 | 128.4 | 131.1 | 163.0 | 167.3 |

|  | Sulfidity, % | | CE, % | | Activity, % | | Causticity, % | |
|---|---|---|---|---|---|---|---|---|
|  | Theoretical | Experimental | Theoretical | Experimental | Theoretical | Experimental | Theoretical | Experimental |
| White Liquor | | | | | | | | |
| #1 | 25.0 | 22.8 | 89.4 | 88.0 | 80.0 | 81.4 | 71.5 | 71.7 |
| #2 | 25.0 | 22.9 | 89.4 | 88.1 | 80.0 | 81.4 | 71.5 | 71.7 |
| #3 | 25.0 | 22.7 | 89.4 | 88.4 | 80.0 | 81.5 | 71.5 | 72.1 |
| #4 | 25.0 | 23.4 | 89.4 | 88.6 | 80.0 | 81.0 | 71.5 | 71.8 |
| #5 | 25.0 | 23.0 | 89.4 | 88.1 | 80.0 | 81.3 | 71.5 | 71.6 |
| #6 | 25.0 | 22.7 | 89.4 | 87.8 | 80.0 | 81.5 | 71.5 | 71.6 |
| #7 | 25.0 | 22.5 | 89.4 | 87.6 | 80.0 | B1.7 | 71.5 | 71.5 |
| #8 | 25.0 | 22.3 | 89.4 | 87.4 | 80.0 | 81.8 | 71.5 | 71.5 |
| #9 | 25.0 | 23.5 | 89.4 | 88.1 | 80.0 | 81.0 | 71.5 | 71.3 |
| #10 | 25.0 | 23.4 | 89.4 | 87.9 | 80.0 | 81.1 | 71.5 | 71.3 |
| Green Liquor | | | | | | | | |
| #1 | 22.1 | 21.5 | 16.9 | 17.9 | 77.9 | 78.5 | 13.2 | 14.1 |
| #2 | 22.1 | 21.0 | 16.9 | 18.1 | 77.9 | 79.0 | 13.2 | 14.3 |
| #3 | 22.1 | 20.7 | 16.9 | 17.5 | 77.9 | 79.3 | 13.2 | 13.8 |

-continued

| | | | | | | | | |
|---|---|---|---|---|---|---|---|---|
| #4 | 22.1 | 20.6 | 16.9 | 17.6 | 77.9 | 79.4 | 13.2 | 14.0 |
| #5 | 22.1 | 21.9 | 16.9 | 16.8 | 77.9 | 78.1 | 13.2 | 13.1 |
| #6 | 22.1 | 21.9 | 16.9 | 16.7 | 77.9 | 78.1 | 13.2 | 13.0 |
| #7 | 22.1 | 21.9 | 16.9 | 16.7 | 77.9 | 78.1 | 13.2 | 13.1 |
| #8 | 22.1 | 21.3 | 16.9 | 16.8 | 77.9 | 78.7 | 13.2 | 13.3 |
| #9 | 22.1 | 21.2 | 16.9 | 16.4 | 77.9 | 78.8 | 13.2 | 13.0 |
| #10 | 22.1 | 21.9 | 16.9 | 16.3 | 77.9 | 78.1 | 13.2 | 12.8 |

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method of determining chemical species in a boron-containing alkaline wood pulping liquor sample comprising the steps of:
   (i) subjecting a first aliquot portion of the boron-containing sample to a primary acid titration analysis to derive multiple equivalence points at different respective pH values;
   (ii) subjecting a second aliquot portion of the boron-containing sample to an analysis by an analytical method other than acid titration, to determine the quantitative presence of boron or sulfide ions therein; and then
   (iii) determining algorithmically the quantitative presence in the boron-containing sample of at least one additional chemical species selected from the group consisting of metaborate, carbonate, hydroxide and sulfide species, other than the chemical species determined in step (ii), based on the combined analytical results of steps (i) and (ii), thereby overcoming interference due to the presence of boron in the sample.

2. The method of claim 1, further comprising the step of (iv) deriving wood pulping parameters on the basis of said quantitative presence of said species determined according to step (iii).

3. The method of claim 1, wherein step (ii) includes analyzing the sample for sulfide ion content using a secondary silver sulfide precipitation titration analysis.

4. The method of claim 3, wherein said primary acid titration analysis and said secondary silver sulfide precipitation titration analysis are performed substantially simultaneously.

5. The method of claim 4, wherein said primary acid titration analysis and said secondary silver sulfide precipitation titration analysis are each carried out on separate independent autotitration units.

6. The method of claim 5, wherein the separate independent autotitraton units are electronically coupled.

7. The method of claim 6, wherein step (iii) is performed by at least one of the autotitration units.

8. The method of claim 7, further comprising the step of (iv) deriving wood pulping parameters on the basis of said quantitative presence of said species determined according to step (iii).

9. The method of claim 8, wherein the wood pulping parameters are calculate automatically by at least one of the autotitration units.

10. The method of claim 1, wherein step (ii) includes analyzing the sample for boron content using atomic spectroscopy.

11. The method of claim 1, wherein step (ii) includes analyzing the sample for boron content using colorimetry.

12. The method of claim 1, wherein step (i) includes determining three pH inflection endpoints at a pH of 10.0–11.0, pH of 7.5–8.5 and pH of 4.0–5.5, respectively.

13. The method of claim 12, wherein step (ii) Includes analyzing the sample for sulfide ion content using a secondary silver sulfide precipitation titration analysis.

14. The method of claim 13, wherein said primary titration analysis and said secondary silver sulfide precipitation titration analysis are performed substantially simultaneously.

15. The method of claim 12, wherein stop (ii) includes analyzing the sample for boron content using atomic spectroscopy.

16. The method of claim 12, wherein step (ii) Includes analyzing the sample for boron content using colorimetry.

* * * * *